US007860695B2

(12) United States Patent  
Fitch et al.

(10) Patent No.: US 7,860,695 B2
(45) Date of Patent: Dec. 28, 2010

(54) METHOD OF CREATING A LOAD BALANCED SPATIAL PARTITIONING OF A STRUCTURED, DIFFUSING SYSTEM OF PARTICLES

(75) Inventors: Blake G. Fitch, White Plains, NY (US); Robert S. Germain, Larchmont, NY (US); Michael C. Pitman, Wappingers Falls, NY (US); Aleksandr Rayshubakly, Tarrytown, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/173,070

(22) Filed: Jul. 15, 2008

(65) Prior Publication Data

US 2008/0300839 A1  Dec. 4, 2008

Related U.S. Application Data

(63) Continuation of application No. 11/392,405, filed on Mar. 29, 2006, now abandoned.

(51) Int. Cl.
*G06G 7/48* (2006.01)
*G06F 7/60* (2006.01)
(52) U.S. Cl. .............................. 703/6; 703/2
(58) Field of Classification Search ............. 703/6, 703/11, 2
See application file for complete search history.

(56) References Cited

PUBLICATIONS

Nyland et al., Achieving Scalable parallel Molecular Dynamics Using Dynamic Spatial Domain Decomposition Techniques, 1997, Journal of Parallel and Distributed Computing, vol. 47, pp. 125-138.*
Nakano, Aiichiro, Multiresolution Load Balancing in Curved Space: the wavelet representation, 1999, Concurrency: Practice and Experience, vol. 11, pp. 343-353.*
T. P. Straatsma, J. A. McCammon, "Load balancing of molecular dynamics simulation with NWChem." 2001.*

* cited by examiner

*Primary Examiner*—Paul L Rodriguez
*Assistant Examiner*—Eunhee Kim
(74) *Attorney, Agent, or Firm*—Scully, Scott, Murphy & Presser, P.C.; Vazken Alexanian (57) ABSTRACT

A method and system are disclosed for creating a load balanced spatial partitioning of a structured, diffusing system of particles with pairwise interactions that is scalable to a very large number of nodes and has favorable communications characteristics including well defined bounds on the number of hops and the number of nodes to which a particle's position must be sent. To deal with structural imbalance, a weight is assigned corresponding to the computational cost for a particular pair interaction of particles or locally clustered groups of particles to simulation space at the midpoint of the distance between the particles or centers of the clusters. A spatial partitioning of the simulation volume is then carried out using a k-d tree or optimal recursive bisection (ORB) to divide the volume into sections that have approximately equal total weights.

19 Claims, 6 Drawing Sheets

DATA STRUCTURE INITIALIZED WITH LINKED LIST OF NODES BELONGING TO THE INTERACTION LOOP DEFINED BY A PAIR OF NODES WITHIN CUT-OFF. THE LISTS REPRESENT THE POSSIBLE LOCATIONS FOR CALCULATING THE INTERACTIONS BETWEEN PARTICLES LOCATED WITHIN THE VOLUME ELEMENTS "OWNED" BY EACH NODE PAIR. IN THIS DATA STRUCTURE, THE ENTRIES ARE SORTED BY NUMBER OF OPTIONS (LENGTH OF LIST) WITH THE ENTRIES POSSESSING THE FEWEST OPTIONS COMING FIRST.

METHOD OF CREATING A LOAD BALANCED SPATIAL PARTITIONING OF A STRUCTURED, DIFFUSING SYSTEM OF PARTICLES

CROSS-REFERENCE TO RELATED APPLICATION

This application is a continuation application of application Ser. No. 11/392,405, filed Mar. 29, 2006, now abandoned, entitled "Reduced Message Count for Interaction Decomposition of N-Body Simulations", the disclosure of which is herein incorporated by reference in its entirety.

BACKGROUND OF THE INVENTION

1. Field of the Invention

This invention generally relates to methods and systems for solving N-body problems, such as classical molecular dynamics. More specifically, the invention relates to methods and systems for creating a load balanced spatial partitioning of a structured, diffusing system of particles.

2. Background Art

Over the last few years, unprecedented computational resources have been developed, such as the Blue Gene computing system family of computers from the International Business Machines Corporation. These resources may be used to attack, among other issues, grand challenge life sciences problems such as advancing the understanding of biologically important processes, in particular, the mechanisms behind protein folding.

In order to address this goal, attention has been directed to creating a classical molecular dynamics software package for long-time and large-scale molecular simulations. Classical molecular dynamics is predominantly an N-body problem. A standard definition of an n-body problem is as follows:

The n-body problem is the problem of finding, given the initial positions, masses, and velocities of n bodies, their subsequent motions as determined by classical mechanics.

An N-body problem, for example molecular dynamics (MD), proceeds as a sequence of simulation time steps. At each time step, forces on particles, in MD atoms, are computed; and then the equations of motion are integrated to update the velocities and positions of the particles. In order to compute the forces on the particles, nominally the force between each particle and every other particle is computed, a computational burden of $O(n^2)$.

Practically speaking, molecular dynamics programs reduce the $O(n^2)$ by cutting off pair interactions at some distance. However for many scientifically relevant molecular systems, the computational burden due to the particle pair interactions remains large. In order to reach scientifically relevant simulation times, parallel computers are required to compute particle pair interactions rapidly.

SUMMARY OF THE INVENTION

An object of this invention is to provide a method for solving N-body problems such as classical molecular dynamics.

Another object of the present invention is to solve the N-body problem by geometrically mapping simulation space to a torus/mesh parallel computer's node space.

A further object of the invention is to enable the geometric n-body problem to be efficiently mapped to a machine with a fundamentally geometric processor space.

Another object of the invention is to create a load balanced spatial partitioning of a structured, diffusing system of particles with pairwise interactions that is scalable to a very large number of nodes and has favorable communications characteristics, including well defined bounds on the number of hops and the number of nodes to which a particle's position must be sent.

These and other objectives are attained with a method of and a system for creating a load balanced spatial partitioning of a structured, diffusing system of particles. The method comprises the steps of providing a computer system having a plurality of processing nodes; assigning computational weights to the particles; separating said system of particles, based on the computational weights assigned to the particles, into a number of voxels; and mapping each voxel to one of the processing nodes of the computer system. For each voxel, the processing node, to which said each voxel is mapped, performs a series of calculations for the particles in said each voxel.

The preferred embodiment of the invention, described below in detail, provides a method and system for creating a load balanced spatial partitioning of a structured, diffusing system of particles with pairwise interactions that is scalable to a very large number of nodes and has favorable communications characteristics including well defined bounds on the number of hops and the number of nodes to which a particle's position must be sent. To deal with structural imbalance, a weight corresponding to the computational cost for a particular pair interaction of particles or locally clustered groups of particles, is assigned to simulation space at the midpoint of the distance between the particles or centers of the clusters. Then a spatial partitioning of the simulation volume is carried out using a k-d tree or optimal recursive bisection (ORB) to divide the volume into sections that have approximately equal total weights. To deal with local degradation of the load balance caused by changes in the distribution of particles from that used to determine the original spatial decomposition one can assign the actual computation of the pair interaction between two particles to any node that has the positions of both particles.

Because pair interactions are cut-off beyond a defined radius $R_c$, one can broadcast the position of a particle to the group of nodes containing a portion of the surface of a suitable specified convex shape that contains the sphere of radius $R_b \geq R_c/2$ centered about the position of original particle in simulation space, ensuring the existence of at least one node containing the positions of both particles required to compute any interaction. An example of such a convex shape is the spherical surface of radius $R_b$ itself. The locus of points formed by the intersection of the two surfaces may be referred to as the "interaction loop", and any node containing a portion of the "interaction loop" can compute the specified interaction. This provides an opportunity for eliminating imbalances caused by short-term local fluctuations in interaction workload. Because the load-balancing is carried out using interaction centers, there are many more geometrically distinct work objects that can be partitioned using an ORB strategy, and this decomposition allows productive use of more nodes than there are particles in the system.

Any suitable computer or computer system may be used to implement the invention; and for instance, the above-mentioned Blue Gene computing system family of computers may be used. The Blue Gene/L parallel computational platform does interprocessor communication primarily using a 3D torus network. Processor space is defined by the location of processors on the 3D torus network and communication costs between processors increase with distance. The methods described herein enable the geometric n-body problem to be efficiently mapped to a machine with a fundamentally geometric processor space, however these methods may be applied to other network topologies with good results.

This invention addresses a method for solving N-body problems such as classical molecular dynamics on preferably mesh/torus machines such as the Blue Gene/L computing system.

In the discussion herein, the following definitions/conventions are used:

For some n-body simulations, it is convenient to define a partitioning of the particles into groups of one or more particles that are treated as a unit for certain purposes. When this intended, the term "fragment" will be used to indicate such an entity that consists of one or more particles.

The term "node" refers to the computational element that form nodes in the graph defined by the interconnection network. Any "node" may include one or more processors. Any suitable processing unit or units may be used in the node, and it is not necessary to describe the detail of the processing units.

The term "simulation space" refers to the domain of the n-body simulation.

The term "node space" refers to the geometry of the interconnections between nodes of the machine. Typically the discussion herein refers to a machine with a three-dimensional torus/mesh interconnect geometry in which each node is connected to its six nearest neighbors and is addressed by a triple of integers that represent its coordinates within the network. In a torus, periodic boundary conditions are implemented physically by connecting the nodes on opposite "faces" of the machine.

Further benefits and advantages of the invention will become apparent from a consideration of the following detailed description, given with reference to the accompanying drawings, which specify and show preferred embodiments of the invention.

DETAILED DESCRIPTION OF THE PREFERRED EMBODIMENTS

Figure 1:
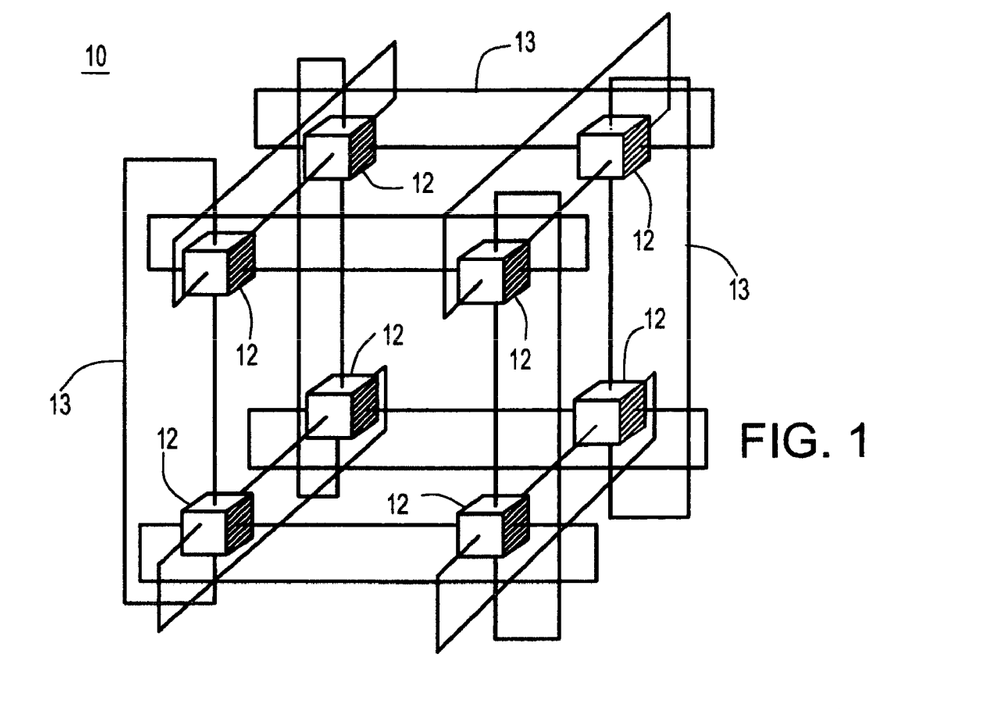
FIG. 1 illustrates a part of a torus computer system that may be used to practice this invention.

FIG. 1 illustrates a part of a computer system or structure that may be used in the implementation of the present invention. More specifically, FIG. 1 shows a part of a Massively Parallel Supercomputer architecture in the form of a three-dimensional torus designed to deliver processing power on the order of teraOPS (trillion floating-point operations per second) for a wide range of applications. The Massively Parallel supercomputer architecture, in an exemplary embodiment, may comprise 65,536 processing nodes organized as a 64×32×32 three-dimensional torus with each processing node connected to six (6) neighboring nodes.

In particular, FIG. 1 shows a torus comprised of eight nodes 12 connected together by links or connections 13. It is clear to see how this interconnect scales by increasing the number of nodes 12 along all three dimensions. With current technology, this architecture can be leveraged to hundreds of teraOPS. As will be understood by those of ordinary skill in the art, other computer structures may also be used in the practice of this invention.

The present invention efficiently solves the N-body problem by, in the preferred embodiment, geometrically mapping simulation space to a torus/mesh parallel computer's node space, a spatial decomposition. In the preferred embodiment, the mechanism for distributing the work is a broadcast of particle positions followed possibly by a reduction of forces on fragment home nodes.

A basic requirement of this method is the ability to broadcast data from one node to a subset of all the nodes in the system. The required collective operations can be constructed using point-to-point communications however; hardware may offer features to enhance the performance of these primitives such as multi-cast.

In the preferred mapping of simulation space to node space, simulation space is divided into the same number of sub-volumes as there are nodes, and further, the simulation space preferably has the same extents (measured in voxels) in each dimension as node space (measured in nodes). The volume elements assigned to each processor (or voxels) may be of non-uniform size.

The two communications operations of interest are:

Surface broadcast: given a convex shape in simulation space, broadcast data from the node containing the center of such a shape to each node managing a portion of the surface of that shape.

Ellipsoidal reduce: given a convex shape in simulation space, theta-reduce data from each node managing a portion of the surface of that shape 20 the root node containing the center of the shape.

N-Body Spatial Decomposition for Load Balance

N-body problems in a periodic simulation space nominally have a computational burden defined by the order $O(N^2)$ pairwise particle interactions possible. In many applications, this computational burden is reduced to $O(N)$ by cutting off interactions between particles separated by more than a specified distance in periodic simulation space.

A natural way to map a spatial problem on a spatial connected machine is with a direct mapping, where the simulation space is uniformly assigned to processors space. For N-body systems (assuming that all pair interactions have the same computational cost) with a uniform density of particles or where no cut-offs are imposed, this simple mapping will result in a balanced load across the machine since each node or region of nodes will have roughly the same interaction computation workload.

Where particles are not evenly distributed in the simulation space and interaction cutoffs are in effect and/or interaction computation costs are not the same, a direct mapping results in load imbalance. There are techniques for locally averaging load imbalance between nodes. However, if the imbalance is severe enough, these regional averaging techniques will be ineffective.

Figure 2:
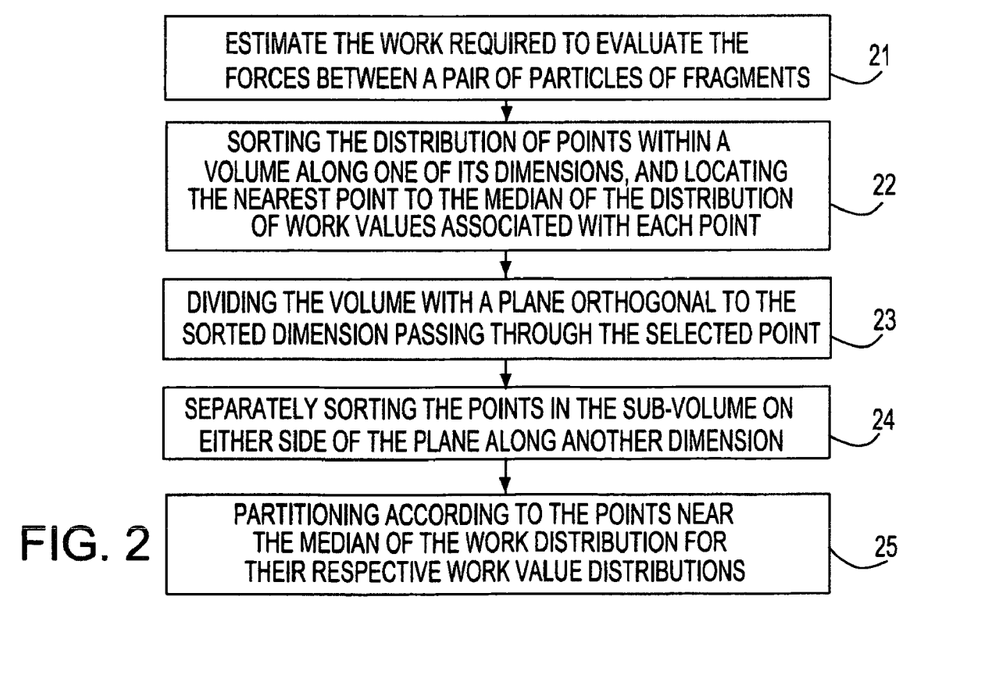
FIG. 2 is a flow chart showing a procedure for partitioning simulation space.

For any fixed distribution of particles, techniques such as optimal recursive bisection (ORB) can be used to balance computational burden on each node by assigning partitioning simulation space into non-uniform sub-volumes that will be assigned to nodes. One suitable spatial decomposition procedure is shown in FIG. 2.

An ORB can be constructed from a distribution of points representing particle or fragment centers, or as discussed below, midpoints of pair interactions. Prior to ORB construction, a function estimating the work associated with each point is evaluated, at step 21, and stored with the point. In the case of pair interaction midpoints, this corresponds to the work required to evaluate the forces between the pair of particles or fragments. ORB construction begins with the periodic boundaries of the simulation cell as the initial volume, and the distribution of points with their associated work values. Application of the ORB technique partitions a unit cell into $2^N$ smaller cells. For cases where N is divisible by 3, the number of sub-volumes will be equal in each dimension (number of sub-volumes=8, 64, 512, 4096, . . .).

The simulation cell volume is partitioned recursively in cycles. Each cycle bisects a volume along each dimension in succession giving eight sub-volumes at the end of the cycle. Each bisection begins, at step 22 of FIG. 2, by sorting the distribution of points within the volume along one of its dimensions and locating the nearest point to the median of the distribution of work values associated with each point. The volume, at step 23, is then divided with a plane orthogonal to the sorted dimension passing through the selected point. The points in the sub-volumes on either side of the plane are, at step 24, then each separately sorted along another dimension, and partitioned according to the points near the median of the work distribution for their respective work value distributions. At step 25, each of the four resulting subvolumes is then sorted in the final dimension and partitioned, giving eight partitions of the original volume. This cycle repeats recursively for each of the eight sub-volumes until the desired number of sub-volumes is reached, which is equal to the number of nodes to be used in the simulation. For cases where N is not divisible by three, the initial cycle partitions along either one or two dimensions, rather than three. The remaining cycles will then partition along each of the three dimensions.

The resulting ORB partitioning of simulation space greatly reduces the variance of work needed to compute the forces represented by the points in a given sub-volume. The assignment of the work represented by the points in each sub-volume to a node therefore provides an initial step in load balancing. A given N-body problem may require multiple load balancing techniques. An ORB may be required to balance the global imbalance caused by the structure of the system being simulated and a local work exchange scheme may be required for imbalances caused by diffusion.

Preferred Load Balancing Algorithm

Figure 3:
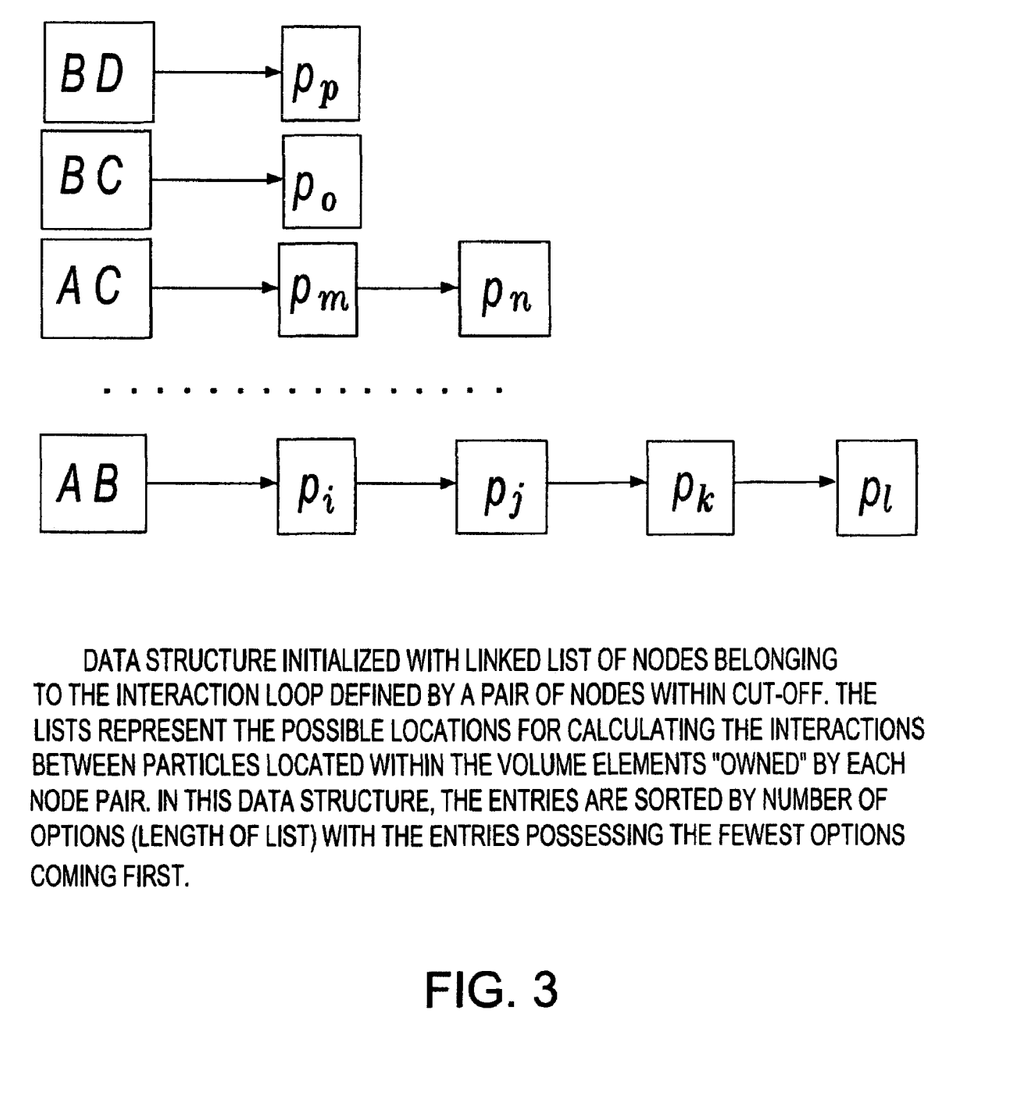
FIG. 3 shows a series of data structures initialized with a linked list of nodes.

In practice, a different scheme for load balancing has been found to be more useful. In this algorithm, space is divided into equally sized volume elements that map simulation space "naturally" onto node space in the way that would be obtained via the ORB technique if load were uniformly distributed throughout the simulation volume. The algorithm begins with creation of a table, the option table with an entry for every pair of nodes whose volume elements have some region within cut-off. To this entry is attached a list of nodes who are members of the interaction loop defined by the intersection of the spherical surfaces with radius equal to half the cut-off distance. The entries in the table are then sorted by length of list with the entries possessing the shortest lists coming first as shown in FIG. 3.

Figure 4:
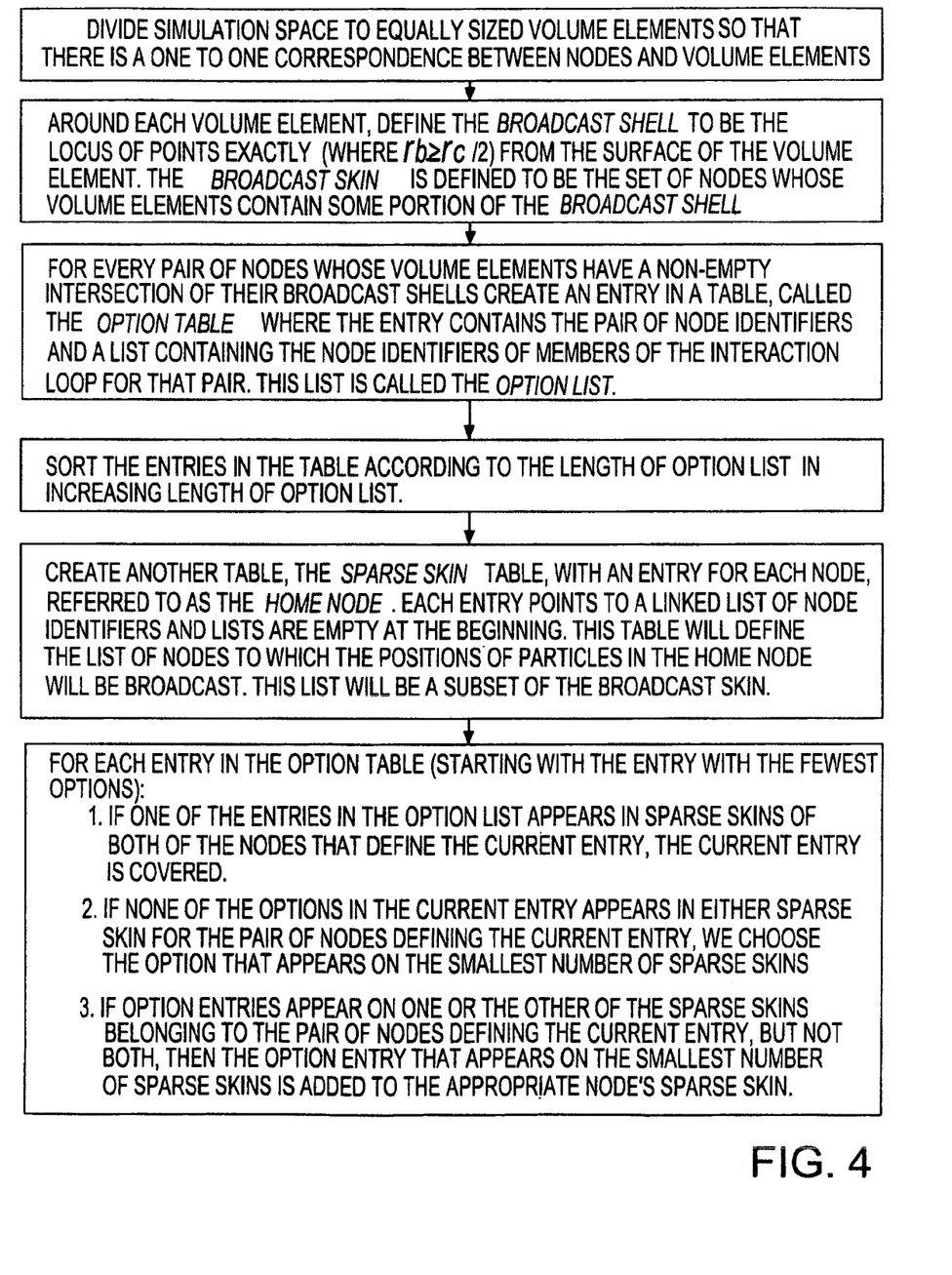
FIG. 4 outlines a procedure to populate a table referred to as the sparse skin table.

An additional table is created that consists of one entry for every node where each entry has an attached list of nodes that comprise the set of nodes to which the positions of particles homed in the originating node is broadcast. However, the table is created with these lists initialized to be empty. Because the lists in this table will be subsets of the full broadcast skins defined by the geometries of the simulation and node spaces, we refer to this as the sparse skin table. Following the description in FIG. 4, we iterate through the option table to populate the sparse skin table. Many variants of the scheme outlined in FIG. 4 are possible including the inclusion of a weighting field in the option table that could be computed, for example, from the actual count of particle pairs within range for each pair of nodes/volume elements. Algorithms applicable to the "bin-packing" problem could be adapted for use in this load-balancing problem.

Figure 5:
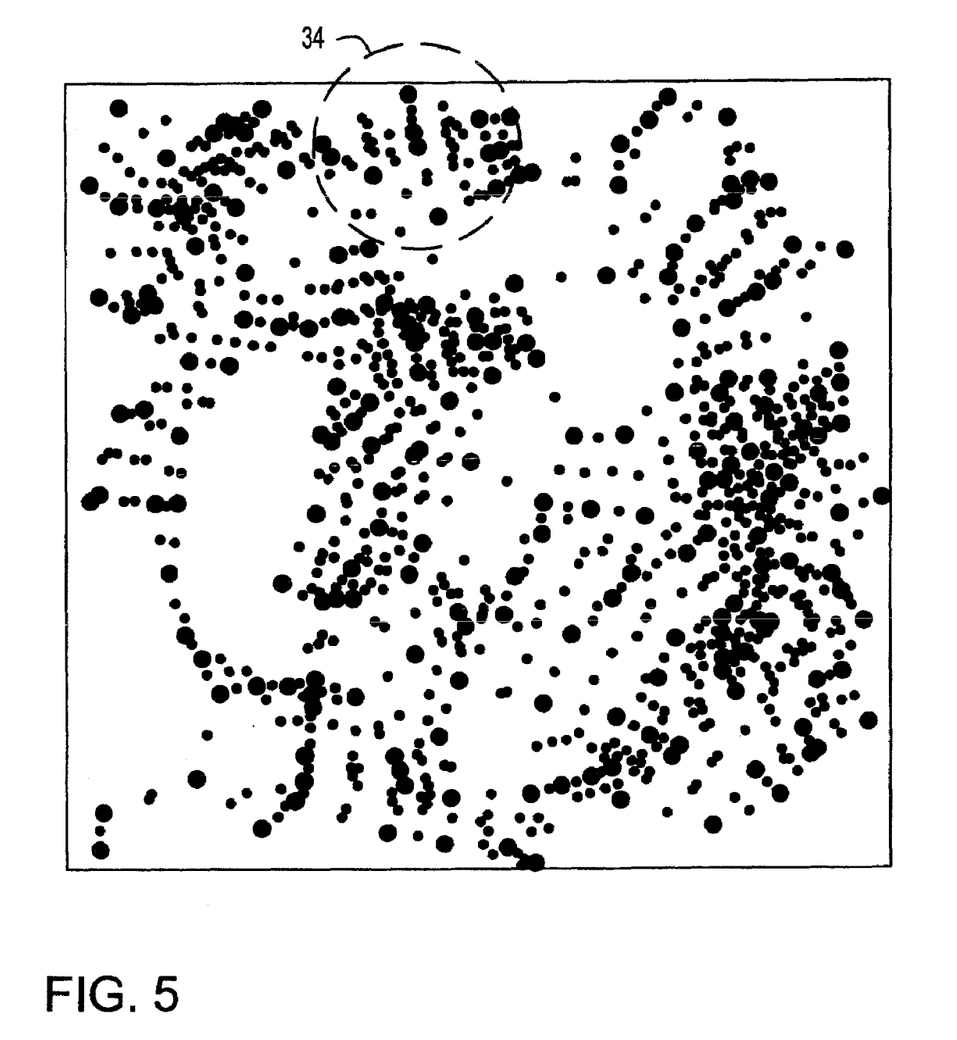
FIG. 5 illustrates the relationship of particle positions and interaction centers in simulation space.

Molecular Dynamics Decompositions Based on Ellipsoidal Communications Primitives Optimal Interaction Assignment Using ORBs and Dynamic Interaction Balancing Molecular dynamics as applied to biomolecular simulation of fixed sized problems on very large, geometric node spaces requires a simulation space to node space mapping that, preferably, maintains as much locality as possible while balancing workload. This is so communication costs and computational costs are minimized in balance. Since the n-body problem may have structural imbalance caused by inhomogeneities in the system, create a partition of simulation based on ORB that divides the workload evenly assuming a nominal weight for each pair interaction and a specified cutoff. In the limit that the ratio of the number of particles to node count is small, it may be desirable to start dividing simulation space using optimal recursive bisection and then switch to a strict volumetric bisection near the leaves to improve micro level balance of particle assignment. FIG. 5 contains a view of a two-dimensional system with both particle positions and interaction centers shown.

More specifically, FIG. 5 illustrates the relationship of the particle positions (larger dots) and the interaction centers (smaller dots) in simulation space. The interaction centers are placed at the mid-point between each pair of particles that fall within the cut-off radius. A dashed circle 34 with radius equal to the cut-off radius chosen is drawn around one of the particles. Static or "structural" load balancing is carried out by using optimal recursive bisection to partition the simulation volume into sub-volumes that contain approximately equal computational burdens. The computational burden of a sub-volume is computed by summing the computational burden of each interaction center contained within that sub-volume.

Next, the minimal set of communicating nodes for a particular particle must be identified. The minimal set of communicating nodes is defined as all those nodes which contain any of the surface of a specified convex volume containing the spherical volume of space (with radius greater than half the cutoff radius) centered about the particle. This defines a minimal volume in node space that ensures that there exists at least one node for every pair of particles within cutoff that can calculate the interaction between that pair.

During each simulation step, each node sends all its particle positions to each of its communication partners and receives from each a set of particle positions. A node may be assigned to evaluate the interaction between any pair of particles in the set of positions it has received.

Figure 6:
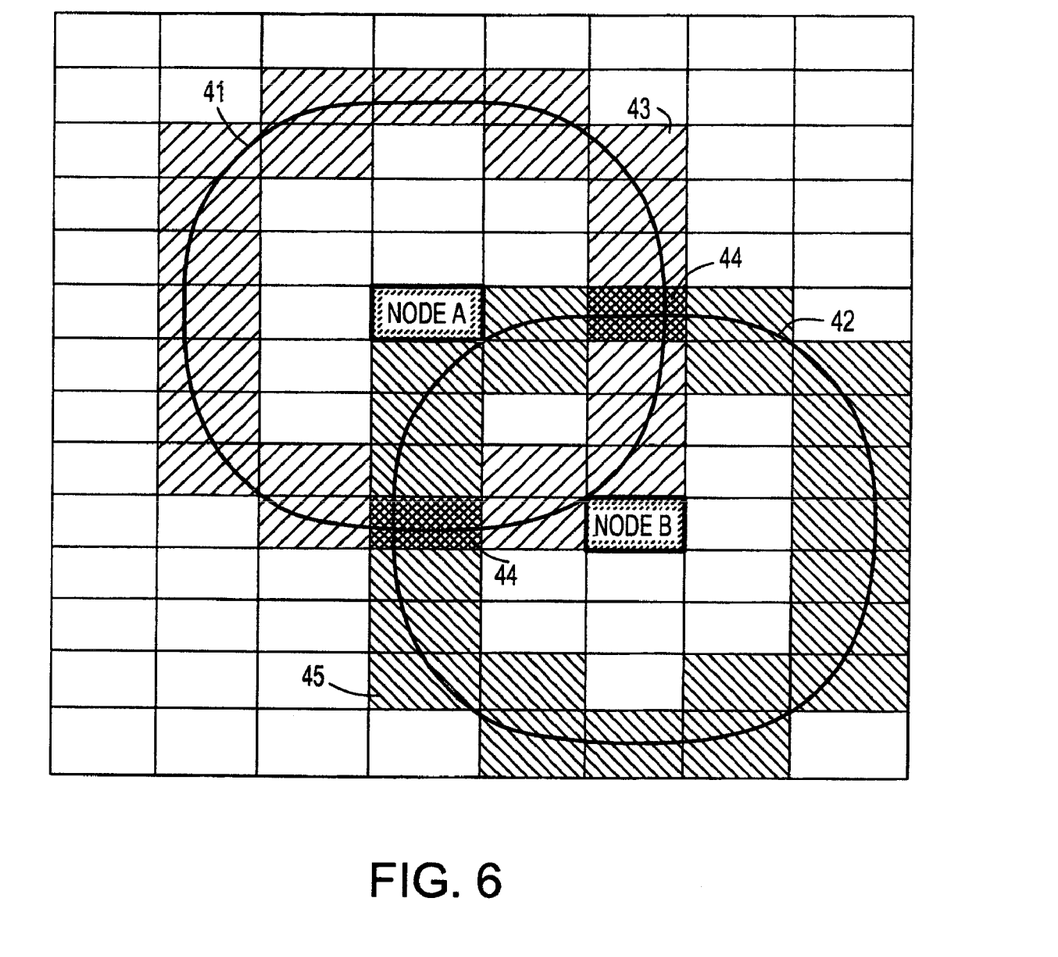
FIG. 6 shows broadcast zones for two nodes.

Although pairs of particle positions in the simulation space separated by close to the cutoff distance might be received by only a single node creating a definitive assignment, generally the positions of any given pair of particles will be received by several nodes as shown in FIG. 6, any one of which may be assigned that pair's interaction.

FIG. 6 shows the broadcast zones 41 and 42 for two nodes superimposed on the spatial decomposition of the domain onto all nodes (two-dimensional view for simplicity). The nodes that contain portions of the surface in simulation space defined by the surface of the volume defined by the set of points within radius $R_b$ of any voxel assigned to Node A are shown in one type of hatching 43 with a different hatching 44 where the nodes also contain portions of the surface in simulation space defined by the surface of the volume defined by the set of points within Rb of any voxel assigned to Node B (which are marked with one type of hatching 45 except where overlap occurs). The broadcast radius $R_b > R_c/2$ where $R_c$ is the cutoff radius. The interaction between a particle stored on Node A and a particle stored on Node B can be computed on any of the nodes with cross-hatching.

Interaction assignment may be accomplished by any method, which results in the interaction between a pair of particles being done once on one node. An example of a suitable algorithm is to specify that the interaction will be done on the node that has received both particle positions and has the minimum node id number. Such algorithms however have load balancing characteristics which reflect the spatial mapping technique used.

In order to reduce micro load imbalance, dynamic deterministic interaction assignment can be employed. These techniques allow rapid overlapping regional averaging. To enable these techniques, each node must measure its current computational load and add this value to each message it sends to its communication partners. When a node receives its set of [load, position set] messages from its communicating partners, it now has enough information to deterministically assign itself a set of interactions. The set of interactions each node can contribute to load averaging among its communication partners.

An example of an algorithm, illustrated in FIG. 7, which allows deterministic, averaged interaction assignment is as follows:

At step 51, receive a complete set of [load, position set] messages from communicating partners. At step 52, for each pair of received messages, create a canonical interaction list including the effects of range cutoffs. At step 53, for each pair of messages received, determine the set of nodes that also received this pair of messages. At step 54, using a deterministic algorithm, assign each interaction (appearing on the canonical interaction list) that could be computed by the above set of nodes to one of those nodes. Examples of such deterministic algorithms include:

Using the loads reported on each of those nodes, assign interactions (which have been ordered in some canonical way) to attempt to equalize the new loads on each of the nodes.
  Randomizing the assignment of interactions to the node set using a hashing algorithm.
  Assigning each interaction to the node owning the voxel that contains the mid-point of the line connecting the interacting pair of particles.

Figure 7:
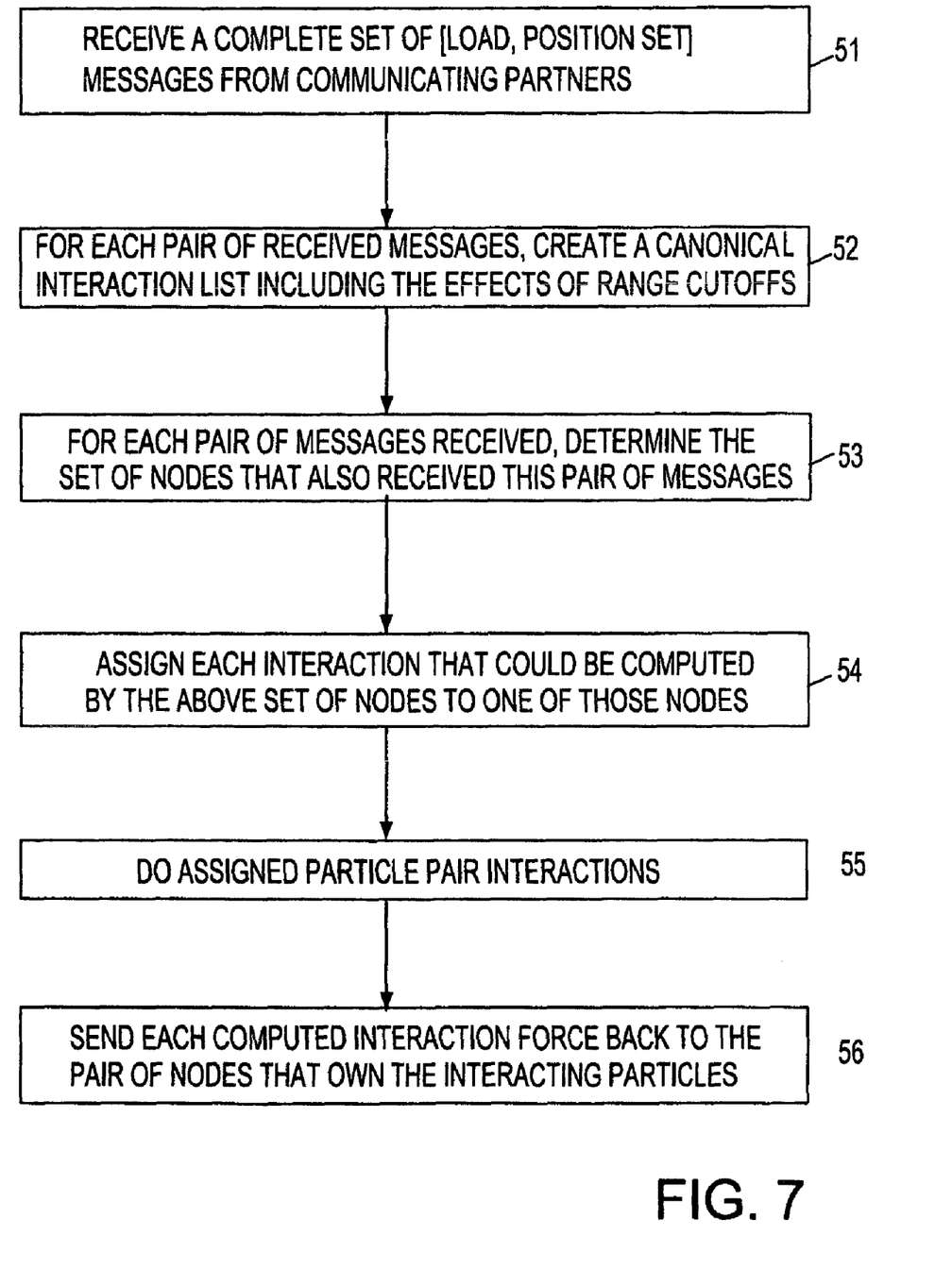
FIG. 7 shows an example of an algorithm that allows deterministic, averaged interaction assignment.

At step 55 of FIG. 7, do assigned particle pair interactions. At step 56, send each computed interaction force back to the pair of nodes that own the interacting particles.

Importantly, this algorithm costs only interaction computation. The cost of returning the force should be added to reflect lower communication cost of computing an interaction on a node which owns one of the particles.

For the purposes of increased scope for load balancing or in cases where communication costs are high relative to computation costs, it may be advantageous to increase the simulation space radius determining the communication partner set beyond $R_c/2$ to increase the number of nodes available for load balancing.

It should be understood that the present invention can be realized in hardware, software, or a combination of hardware and software. Any kind of computer/server system(s)—or other apparatus adapted for carrying out the methods described herein—is suited. A typical combination of hardware and software could be a general purpose computer system with a computer program that, when loaded and executed, carries out the respective methods described herein. Alternatively, a specific use computer, containing specialized hardware for carrying out one or more of the functional tasks of the invention, could be utilized.

The present invention, or aspects thereof, can also be embedded in a computer program product, which comprises all the respective features enabling the implementation of the methods described herein, and which—when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

While it is apparent that the invention herein disclosed is well calculated to fulfill the objects stated above, it will be appreciated that numerous modifications and embodiments may be devised by those skilled in the art, and it is intended that the appended claims cover all such modifications and embodiments as fall within the true spirit and scope of the present invention.

What is claimed is:

1. A method of creating a load balanced spatial partitioning of a structured, diffusing system of particles, comprising the steps of:
  providing a computer system having a plurality of processing nodes;
  assigning computational weights to the particles;
  separating said system of particles, based on the computational weights assigned to the particles, into a number of voxels;
  mapping each voxel to one of the processing nodes of the computer system;
  for each of the processing nodes, specifying a convex volume of space around said each of the processing nodes, said volume of space having a surface, and wherein one or more of the processing units contain a part of said surface;
  for each of the processing nodes, identifying a group of the processing nodes as communication partners of said each node, wherein the communication partners of said each node are all of the processing nodes that contain any of the surface of the specified convex volume around said each node;
  each of the processing nodes, to which one of the voxels is mapped, broadcasting to the communication partners of said each node, the positions of all of the particles in said one of the voxels, and the communication partners of said each node receiving the positions broadcast to said communication partners; and
  calculating interactions between specified pairs of particles of the system of particles by, for each of the specified pairs of particles, using one of the processing nodes that receives the positions of both of the particles of said each specified pair of particles, to calculate an interaction between said each specified pair of particles.

2. A method according to claim 1, wherein:
the step of assigning computational weights includes a step of assigning each of the computational weights to a position in said system; and
the separating step includes the step of separating said system of particles into said number of voxels based on the positions assigned to the computational weights.

3. A method according to claim 2, wherein the voxels have an approximately equal total of computational weights to distribute the computational load of the computer system approximately equally among the processing nodes of the computer system.

4. A method according to claim 2, wherein:
each computational weight is associated with a pair of the particles; and
the step of assigning each of the computational weights to a position includes a step of assigning each computational weight to a position between the pair of particles with which said each computational weight is associated.

5. A method according to claim 1, wherein:
the computer system has a given number of said processing nodes;
said given number of voxels equals said given number; and
the mapping step includes a step of mapping each of the voxels to a respective one of the processing nodes of the computer system.

6. A method according to claim 1, comprising the further step of, over time, assigning said calculations for some of the particles from one of the processing nodes to another of the processing nodes to alleviate reduced load balance caused by changes in the distribution of particles in said system.

7. A method according to claim 1, wherein:
the using step includes a step of using said one of the processing nodes to perform said series of calculations at a first time for the particles in said each voxel; and
comprising the further steps of, for each of at least some of the particles in the system:
broadcasting a position of the particle to a set of said processing nodes; and
using said one of said set of processing nodes to perform said calculations, at a second time.

8. A system for creating a load balanced spatial partitioning of a structured, diffusing system of particles, comprising the steps of:
a computer system having a plurality of processing nodes;
means for assigning computational weights to the particles;
means for separating said system of particles, based on the computational weights assigned to the particles, into a number of voxels; and
means for mapping each voxel to one of the processing nodes of the computer system, wherein said one of the processing nodes performs a series of calculations for the particles in said each voxel; and
wherein the computer system is configured for;
for each of the processing nodes, specifying a convex volume of space around said each of the processing nodes, said volume of space having a surface, and wherein one or more of the processing units contain a part of said surface;
for each of the processing nodes, identifying a group of the processing nodes as communication partners of said each node, wherein the communication partners of said each node are all of the processing nodes that contain any of the surface of the specified convex volume around said each node;
each of the processing nodes, to which one of the voxels is mapped, broadcasting to the communication partners of said each node, the positions of all of the particles in said one of the voxels, and the communication partners of said each node receiving the positions broadcast to said communication partners; and
calculating interactions between specified pairs of particles of the system of particles by, for each of the specified pairs of particles, using one of the processing nodes that receives the positions of both of the particles of said each specified pair of particles, to calculate an interaction between said each specified pair of particles.

9. A system according to claim 8, wherein:
the means for assigning computational weights includes means for assigning each of the computational weights to a position in said system; and
the means for separating includes means for separating said system of particles into said number of voxels based on the positions assigned to the computational weights.

10. A system according to claim 9, wherein the voxels have an approximately equal total of computational weights to distribute the computational load of the computer system approximately equally among the processing nodes of the computer system.

11. A system according to claim 9, wherein:
each computational eight is associated with a pair of the particles; and
the assigning means includes means for assigning each computational weight to a position between the pair of particles with which said each computational weight is associated.

12. A system according to claim 8, wherein:
the computer system has a given number of said processing nodes;
said given number of voxels equals said given number; and
the means for mapping includes means for mapping each of the voxels to a respective one of the processing nodes of the computer system.

13. A system according to claim 8, wherein:
said one of the processing nodes performs said series of calculations at a first time for the particles in said each voxel; and further comprising:
means for broadcasting the positions of at least some of the particles to a set of said processing nodes; and wherein one of said set of processing nodes performs said series of calculations at a second time.

14. A program storage device readable by machine, tangibly embodying a program of instructions executable by the machine to perform method steps for creating a load balanced spatial partitioning of a structured, diffusing system of particles, and
for use with a computer system having a plurality of processing nodes, said method steps comprising:
assigning computational weights to the particles;
separating said system of particles, based on the computational weights assigned to the particles, into a number of voxels;
mapping each voxel to one of the processing nodes of the computer system;
for each of the processing nodes, specifying a convex volume of space around said each of the processing nodes, said volume of space having a surface, and wherein one or more of the processing units contain a part of said surface;

for each of the processing nodes, identifying a group of the processing nodes as communication partners of said each node, wherein the communication partners of said each node are all of the processing nodes that contain any of the surface of the specified convex volume around said each node; each of the processing nodes, to which one of the voxels is mapped, broadcasting to the communication partners of said each node, the positions of all of the particles in said one of the voxels, and the communication partners of said each node receiving the positions broadcast to said communication partners; and calculating interactions between specified pairs of particles of the system of particles by, for each of the specified pairs of particles, using one of the processing nodes that receives the positions of both of the particles of said each specified pair of particles, to calculate an interaction between said each specified pair of particles.

15. A program storage device according to claim 14, wherein:

the step of assigning computational weights includes a step of assigning each of the computational weights to a position in said system; and the separating step includes a step of separating said system of particles into said number of voxels based on the positions assigned to the computational weights.

16. A program storage device according to claim 15, wherein the voxels have an approximately equal total of computational weights to distribute the computational load of the computer system approximately equally among the processing nodes of the computer system.

17. A program storage device according to claim 15, wherein:

each computational weight is associated with a pair of the particles; and the step of assigning each of the computational weights to a position includes the step of assigning each computational weight to a position between the pair of particles with which said each computational weight is associated.

18. A program storage device according to claim 14, wherein:

the computer system has a given number of said processing nodes;

said given number of voxels equals said given number; and the mapping step includes a step of mapping each of the voxels to a respective one of the processing nodes of the computer system.

19. A program storage device according to claim 14, wherein:

the using step includes a step of using said one of the processing nodes to perform said series of calculations at a first time for the particles in said each voxel; and said method steps comprise the further steps of, for each of at least some of the particles in the system:

broadcasting a position of the particle to a set of said processing nodes; and using said one of said set of processing nodes to perform said calculations at a second time.

\* \* \* \* \*